United States Patent
Cianfrani et al.

(10) Patent No.: US 9,445,842 B2
(45) Date of Patent: Sep. 20, 2016

(54) FACET FIXATION PROSTHESIS

(75) Inventors: Jason Cianfrani, East Norriton, PA (US); Daniel Laskowitz, Lancaster, PA (US); Edward Karpowicz, Swedesboro, NJ (US)

(73) Assignee: Globus Medical, Inc., Audubon, PA (US)

( * ) Notice: Subject to any disclaimer, the term of this patent is extended or adjusted under 35 U.S.C. 154(b) by 813 days.

(21) Appl. No.: 12/359,706

(22) Filed: Jan. 26, 2009

(65) Prior Publication Data

US 2009/0192551 A1 Jul. 30, 2009

Related U.S. Application Data

(60) Provisional application No. 61/023,197, filed on Jan. 24, 2008.

(51) Int. Cl.
| | |
|---|---|
| A61B 17/68 | (2006.01) |
| A61B 17/70 | (2006.01) |
| A61B 17/86 | (2006.01) |

(52) U.S. Cl.
CPC ........... *A61B 17/686* (2013.01); *A61B 17/685* (2013.01); *A61B 17/7064* (2013.01); *A61B 17/8685* (2013.01); *A61B 17/8695* (2013.01)

(58) Field of Classification Search
CPC ............. A61F 2310/00023; A61F 2002/4475; A61F 2/42; A61F 2/30; A61F 2/44; A61F 2/40; A61F 2/38; A61F 2/32; A61B 17/8645; A61B 2/0811; A61B 17/685; A61B 17/686; A61B 17/68; A61B 17/58
USPC ............... 606/279, 301, 305, 268, 289, 290; 623/17.11
See application file for complete search history.

(56) References Cited

U.S. PATENT DOCUMENTS

| | | | |
|---|---|---|---|
| 5,217,462 A * | 6/1993 | Asnis ..................... | A61B 17/74 606/105 |
| 5,527,312 A | 6/1996 | Ray | |
| 5,725,529 A * | 3/1998 | Nicholson .......... | A61B 17/0401 606/232 |
| 5,871,486 A | 2/1999 | Huebner et al. | |
| 5,893,850 A * | 4/1999 | Cachia ................ | A61B 17/683 606/326 |
| 6,030,162 A | 2/2000 | Huebner | |
| 6,074,391 A * | 6/2000 | Metz-Stavenhagen et al. ............................. | 606/278 |
| 6,290,701 B1 * | 9/2001 | Enayati .................. | A61B 17/68 606/325 |
| 6,319,269 B1 | 11/2001 | Li | |
| 6,368,319 B1 * | 4/2002 | Schaefer ......................... | 606/60 |
| 6,485,518 B1 | 11/2002 | Cornwall et al. | |
| 6,540,747 B1 | 4/2003 | Marino | |

(Continued)

FOREIGN PATENT DOCUMENTS

| | | |
|---|---|---|
| WO | 2004008949 A2 | 1/2004 |
| WO | 2004098453 A2 | 11/2004 |

*Primary Examiner* — Christian Cevilla
*Assistant Examiner* — Seema Mathew

(57) ABSTRACT

A facet screw system for surgical implantation into bone tissue having a shaft, a compression member and a washer. The shaft includes a shaft having a bone engaging portion and a compression member engaging portion. The compression member includes a spherical head portion having a recess for engaging with a driving instrument, and an elongated coupling portion having internal threads for coupling with the compression member engaging portion of the shaft and a washer coupled to the spherical head portion of the compression member and having a plurality of bone engaging protrusions. The washer is adapted to be polyaxially rotatable with respect to the compression member.

18 Claims, 10 Drawing Sheets

(56) References Cited

U.S. PATENT DOCUMENTS

| | | | |
|---|---|---|---|
| 6,547,795 B2 | 4/2003 | Schneiderman | |
| 6,616,694 B1* | 9/2003 | Hart | A61B 17/686 606/308 |
| 6,648,893 B2* | 11/2003 | Dudasik | A61B 17/686 606/327 |
| 6,669,698 B1 | 12/2003 | Tromanhauser et al. | |
| 6,808,526 B1 | 10/2004 | Magerl et al. | |
| 6,887,243 B2 | 5/2005 | Culbert | |
| 6,951,561 B2 | 10/2005 | Warren et al. | |
| 6,964,664 B2* | 11/2005 | Freid et al. | 606/281 |
| 6,981,976 B1* | 1/2006 | Schoenefeld | A61B 17/8891 606/104 |
| 7,059,392 B2* | 6/2006 | Kovac | F16B 2/08 165/140 |
| 7,371,238 B2 | 5/2008 | Soboleski et al. | |
| 7,794,484 B2* | 9/2010 | Stone | A61B 17/0401 606/300 |
| 8,043,347 B2* | 10/2011 | Jiang | A61F 2/0811 606/311 |
| 9,119,678 B2* | 9/2015 | Duggal | A61B 17/7064 |
| 2003/0105465 A1* | 6/2003 | Schmieding | A61B 17/0401 606/916 |
| 2003/0149436 A1* | 8/2003 | McDowell | A61B 17/68 606/716 |
| 2004/0260298 A1* | 12/2004 | Kaiser | A61F 2/0811 606/232 |
| 2005/0149030 A1 | 7/2005 | Serhan et al. | |
| 2005/0203522 A1 | 9/2005 | Vaughan | |
| 2006/0085068 A1 | 4/2006 | Barry | |
| 2006/0200137 A1 | 9/2006 | Soboleski et al. | |
| 2006/0276790 A1 | 12/2006 | Dawson et al. | |
| 2007/0112428 A1 | 5/2007 | Lancial | |
| 2007/0118132 A1 | 5/2007 | Culbert et al. | |
| 2008/0269809 A1* | 10/2008 | Garamszegi | A61B 17/7037 606/305 |
| 2008/0306555 A1* | 12/2008 | Patterson | A61B 17/8695 606/303 |
| 2009/0105716 A1* | 4/2009 | Barrus | A61B 17/7032 606/301 |
| 2009/0248089 A1* | 10/2009 | Jacofsky | A61B 17/686 606/311 |
| 2009/0275993 A1* | 11/2009 | Phan | A61B 17/7064 606/315 |
| 2011/0313466 A1* | 12/2011 | Butler | A61B 17/7064 606/279 |
| 2011/0313472 A1* | 12/2011 | Yap | A61B 17/7064 606/305 |
| 2012/0022603 A1* | 1/2012 | Kirschman | A61B 17/7064 606/305 |

* cited by examiner

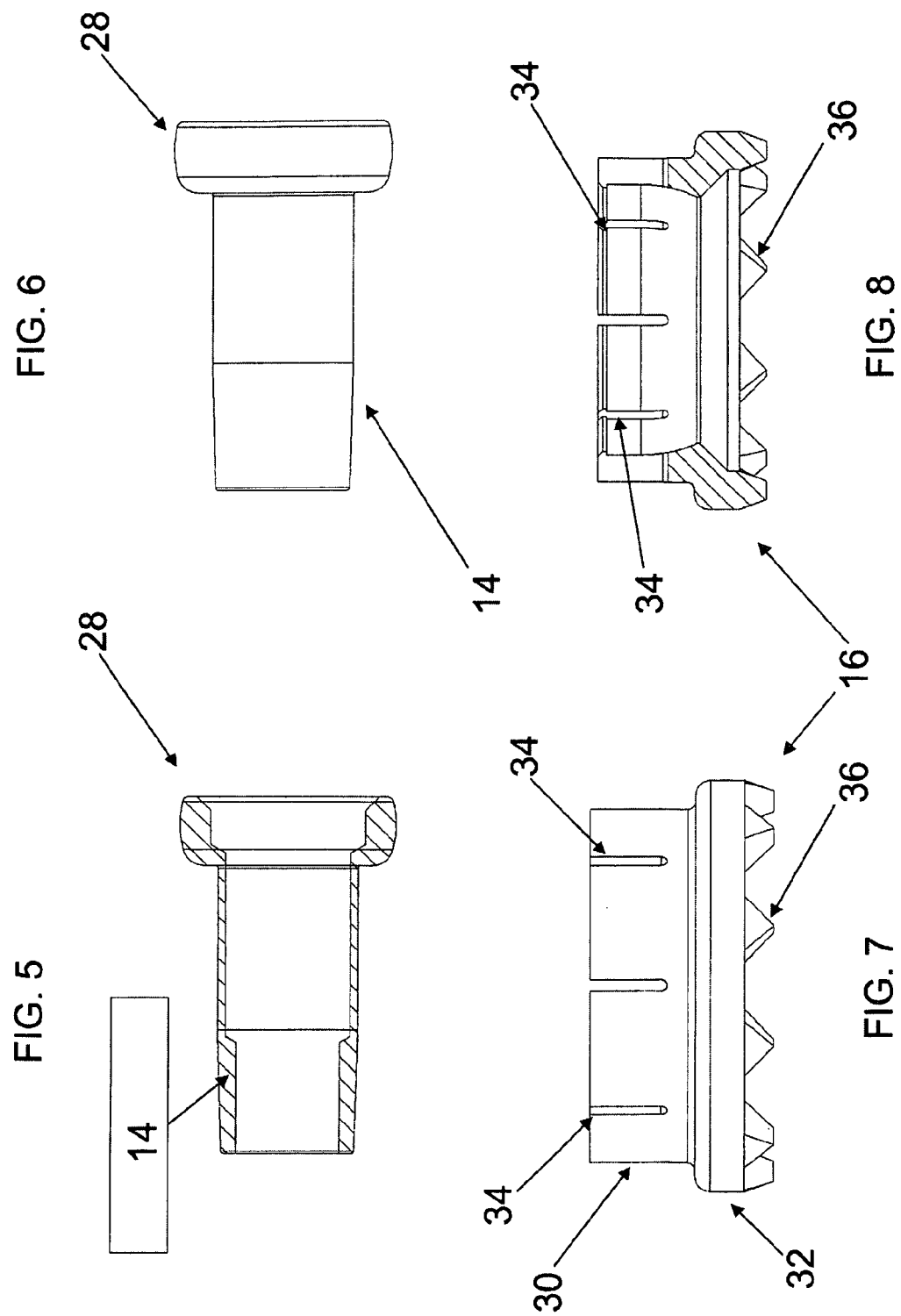

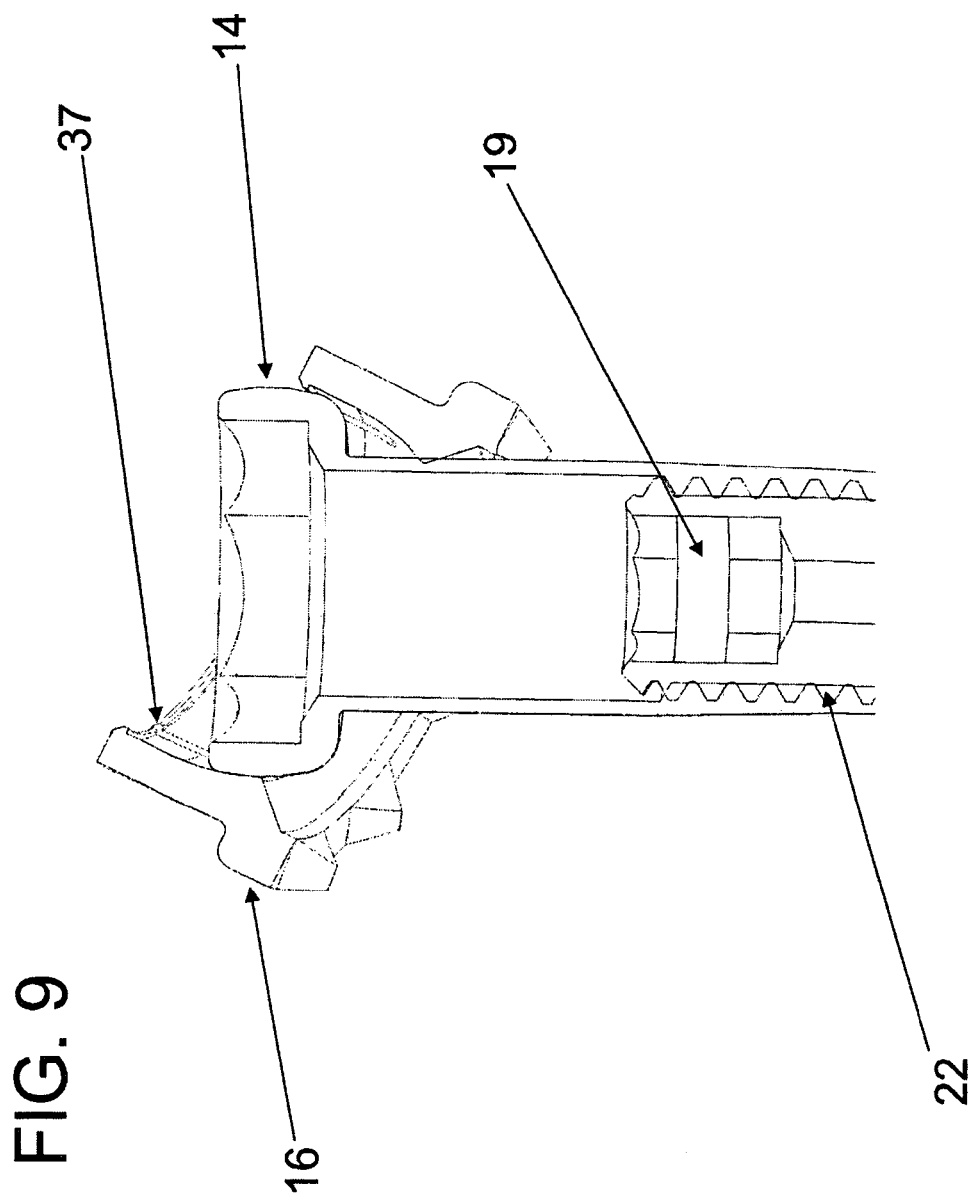

US 9,445,842 B2

FACET FIXATION PROSTHESIS

CROSS-REFERENCE TO RELATED APPLICATIONS

The present application claims the benefit of Provisional Application Ser. No. 61/023,197 filed on Jan. 24, 2008, the contents of which are hereby incorporated by reference in their entirety.

FIELD OF THE INVENTION

The present invention relates to a device to stabilize and support the spine.

CROSS-REFERENCE TO RELATED APPLICATIONS

All publications and patent applications mentioned in this specification are herein incorporated by reference to the same extent as if each individual publication or patent application was specifically and individually indicated to be incorporated by reference.

BACKGROUND OF THE INVENTION

Degenerative disc disease refers to any kind of degradation of the intervertebral disc. Patients suffering from degenerative disc disease with severe or chronic back pain or instability are commonly treaded with spinal fusion. Fusion of the lumbar spine typically involves combining a bone graft/implant with fixation devices to add extra stabilization of the spine while the area heals, increasing the chance of a successful fusion.

Traditionally this fixation is provided by pedicle screws and rods in order to support and stabilize the spine until boney fusion occurs. Pedicle screw fixation has been the gold standard for such stabilization since the late 1980s. However, pedicle screw fixation is invasive and has been shown to injure the paraspinous muscles causing scarring and other complications. Recently facet fixation has grown in popularity as a less invasive means of providing the posterior stabilization necessary in lumbar fusion cases. There is a need in the spine industry for a fast, simple, and minimally invasive means to instrument an interbody fusion involving facet fixation.

SUMMARY OF THE INVENTION

The present invention generally relates to a facet screw system for surgical implantation into bone tissue having a shaft, a compression member and a washer. The shaft includes a shaft having a bone engaging portion and a compression member engaging portion. The compression member includes a spherical head portion having a recess for engaging with a driving instrument, and an elongated coupling portion having internal threads for coupling with the compression member engaging portion of the shaft and a washer coupled to the spherical head portion of the compression member and having a plurality of bone engaging protrusions. The washer is adapted to be polyaxially rotatable with respect to the compression member.

BRIEF DESCRIPTION OF THE DRAWINGS

The invention will be more readily understood with reference to the embodiments thereof illustrated in the attached drawing figures, in which:

FIGS. 5 and 6 illustrate different views of the compression member in accordance with an exemplary embodiment of the invention;

FIGS. 7 and 8 illustrate different views of the washer in accordance with an exemplary embodiment of the invention;

FIG. 9 illustrates the cross-sectional view of the connection between the shaft, the compression member and the washer in accordance with an exemplary embodiment of the invention;

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
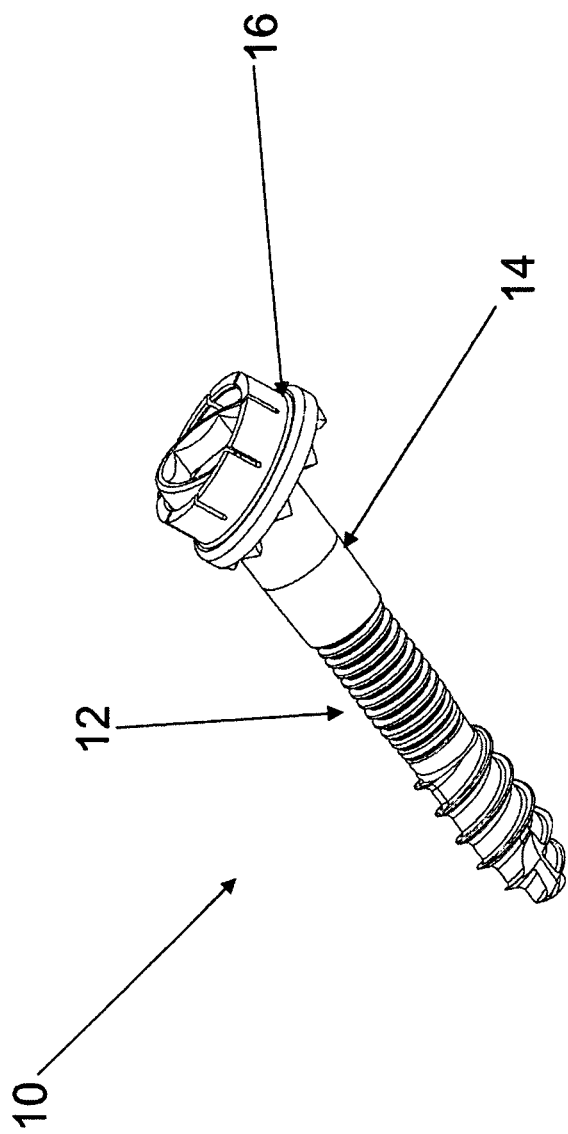
FIG. 1 is a perspective view of a prosthetic device in accordance with an embodiment of the invention.
Figure 2:
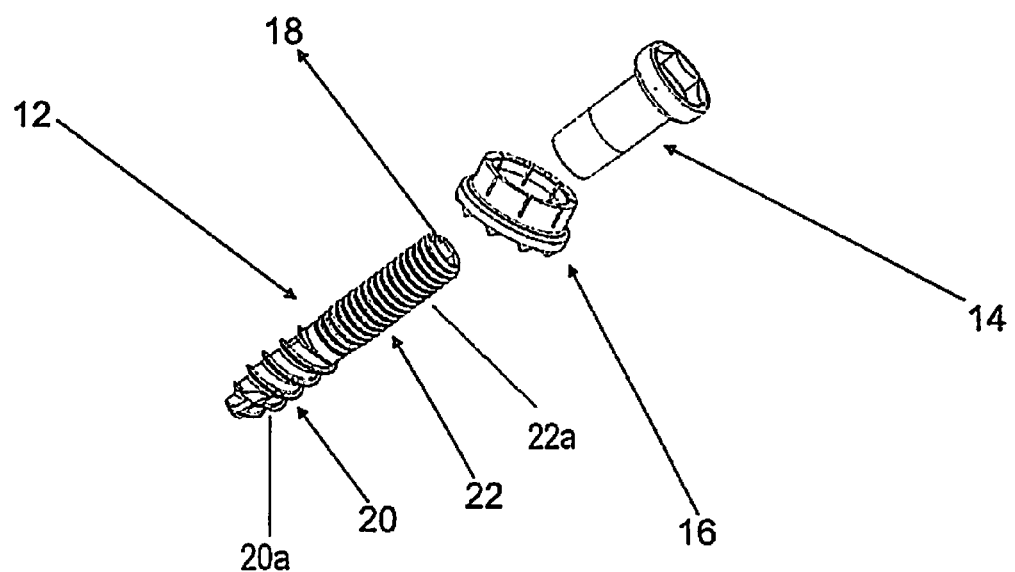
FIG. 2 illustrates the components of the prosthetic device in accordance with an exemplary embodiment of the invention.

With reference to FIGS. 1 and 2, one embodiment of a facet screw system 10 according to the present invention is illustrated. The facet screw system 10 includes a screw shaft 12, a compression member 14, and a washer 16. The facet screw 10 may be constructed from any biocompatible material including, but not limited to, stainless steel alloys, titanium, titanium based alloys, or polymeric materials.

Figure 3:
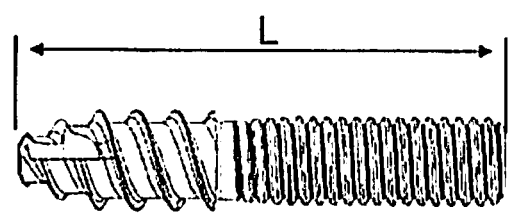
FIG. 3 illustrates the shaft portion of the prosthetic device in accordance with an exemplary embodiment of the invention.

Referring to FIGS. 2 and 3, the compression member 14 has a spherical top portion that is engageable with the spherical curvature of the washer 16. It is also desirable to prevent the compression member from completely passing through the washer 16. This may be achieved by making the diameter of the bottom portion of the washer 16 opening, through which the threaded portion of the shaft may pass, as least between 5% and 10% smaller than the diameter of the spherical top portion of the compression member 14. To permit rotation or swiveling o the shaft relative to the washer 16, the diameter spherical top portion of the compression member may be from about 5% to about 30% less than the diameter of the washer 16 opening.

The shaft 12 which engages with compression member 14 may also include a recess 18 for receiving a driving instrument. As is well known in the art, the recess 18 may be configured and dimensioned to be any shape that corresponds with the end of the driving instrument designed to engage the screw shaft portion 12.

The shaft portion 12 of the facet screw 10 comprises a shaft having a length L surrounded at least in part by a plurality of thread portions 20a, 22a. The shaft having a length L may vary depending upon the anatomy of the spine. The following lengths are provided in a preferable embodiment of the present invention.

| Bone Engaging Portion | Compression Member | Assembled Length with Compression Member |
|---|---|---|
| 10 mm | 15 mm | 30 mm |
| 12.5 mm | 15 mm | 40 mm |
| 15 mm | 15 mm | 50 mm |
| 25 mm | 15 mm | 60 mm |

The diameter of the bone engaging portion 20 is preferably 5.0 mm to 6.0 mm and the compression member engaging portion 22 has a diameter in the range of 4.4 mm to 4.9 mm. In a preferred embodiment, the diameter of the compression member engaging portion 22 remains generally constant from the proximal end toward the distal end of the shaft 12. However, the diameter of the bone engaging portion 20 preferably decreases towards the distal tip 24 of the facet screw 10. The constant diameter of a majority portion of the bone engaging portion 20 allows for optimal screw positioning when the bone screw is inserted into a predetermined area in the bone tissue. In another embodiment, the diameter of the shaft 12 may vary along its length, including increasing in diameter from the proximal end to the distal end or decreasing in diameter from the proximal end to the distal end.

Figure 4:
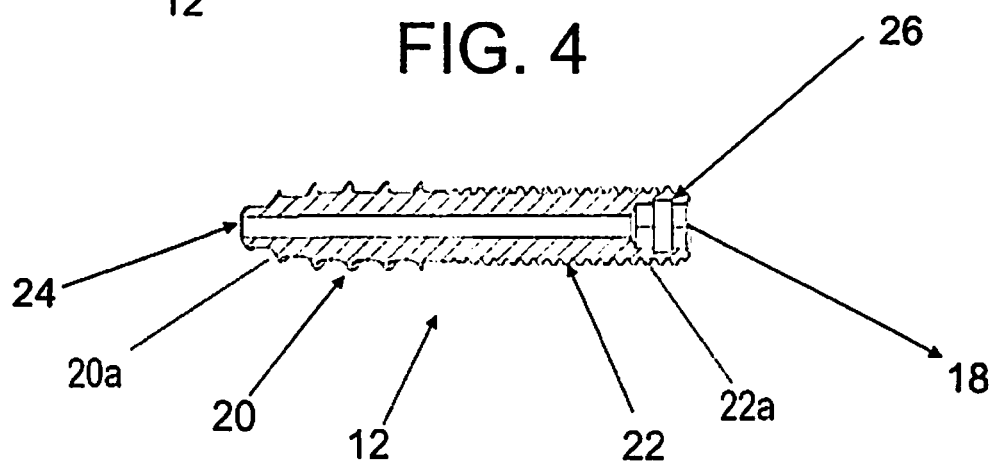
FIG. 4 shows the cross-sectional view of the shaft portion of the prosthetic device in accordance with an exemplary embodiment of the invention.

Looking at FIGS. 3 and 4, the plurality of threads surrounding the shaft 12 extend, in a preferred embodiment, from the distal tip 24 of the shaft 12 to the distal end 26 of the shaft 12. In the preferred embodiment, the threads of the bone engaging portion 20 of the shaft 12 are dual lead thread type and the tube engaging portion 22 are provided with a STD machine thread. However, any type of thread for either portion 20, 22 may be used to facilitate the function of the facet screw 10.

In another preferred embodiment, facet screw 10 may also include at least one flute to clear any chips, dust, or debris generated when the facet screw 10 is implanted into bone tissue. In yet another preferred embodiment, the facet screw 10 may be cannulated so that a guide wire may be used for positioning the facet screw into the bony elements of the spine.

Now turning to FIGS. 5 and 6, the compression member 14 according to the preferred embodiment is illustrated. The compression member 14 preferably has standard female threads that mate with the male threads on the compression member portion 22 of the shaft portion 12 of the facet screw 10. In the preferred embodiment, the compression member 14 is configured and dimensioned with a spherical head 28 having a recess for receiving a driving instrument. The outer diameter of the compression member 14 is preferably the same as the outer diameter of the bone engaging portion 20 of the shaft 12 of the facet screw 10.

When the compression member 14 is rotated clockwise, the compression member 14 advances distally, thereby shortening the length between the bone engaging surface 20 of the shaft portion 12 and the washer 16 of the facet screw 10. During this step, the facet screw 10 is held in place while only the compression member 14 is rotated. As the washer 16 is advanced to contact the facet joint, compression of the facets occurs providing greater stability and fixation of the superior and inferior facets.

FIGS. 7 and 8 illustrate the washer 16 in one embodiment of the present invention. The washer 16 is preferably pre-assembled as a single piece having a flexible portion 30 and bone engaging portion 32. The washer 16 has an opening having a generally spherical curvature which the shaft portion of the facet screw is retained within. It is desirable to prevent the shaft 12 from passing completely through the washer 16. Therefore, a ridge 37 is provided on the inner circumference of the flexible portion 30 of the washer 16.

The flexible portion 30 is provided with a plurality of slits 34 to allow the washer 16 to be flexible or resilient for engaging with the spherical head 28 of the compression member 14. The bone engaging portion 32 is configured and dimensioned with a plurality of protrusions 36 to engage with bone. The spherical head 28 of the compression member 14 and the flexible portion 30 of the washer 16 are configured to angulate with respect to one another. The washer 16 is configured to angulate with respect to the compression member 14, thereby enabling the washer 16 to conform to various angle differences of the superior facet while the facet screw 10 is advanced a different trajectory across the facet joint.

The bone engaging portion 32 of the washer 16 is configured and dimensioned so that any load may be distributed evenly when the shaft portion of the facet screw is inserted at a non-orthogonal angle. In one embodiment, the bottom surface of the washer 16 lies substantially flush with the surface of the bone. In another embodiment, the bone engaging portion 32 is configured with a plurality of protrusions to promote bone contact over a substantial portion of the bottom portion of the bone engaging portion 32 of the washer 16 even when the bony surface contacting the washer is uneven or has a depression in it. In addition, the protrusions 36 may help minimize the potential for screw or compression member back-out.

In another embodiment, each of the plurality of protrusions 36 which engage the bone may be configured to achieve maximum amount of purchase in the bone by providing protrusions that more readily permits sliding in one direction while more substantially resisting motion in a second direction. Thus, angled or curved protrusions may be used and a plurality of them may be oriented on the bottom surface of the crown to permit rotational sliding one direction more readily than in another direction. One advantage of an angled or curved protrusion is that it can be driven into the bone by applying a given amount of torque. Another advantage of an angled or curved protrusion is that it may be configured and dimensioned such that it provides more resistance to motion in one direction than in the other direction.

In some applications, it may be desirable to allow a surgeon to change the geometry of some or all portions of the washer 16 based on the shape of the bone. This provides the advantage of allowing a surgeon to visually inspect the bone and configure the shape of the washer 16 accordingly. It may be desirable to change the shape so that there is increased contact between the bone engaging portion of the washer 16 and the surface of the bone. This is because the load can only be distributed over the areas of washer 16 that in contact with the surface of the bone. An uneven contact with the bone may cause the load to be increased over the areas of the washer 16 that are in contact with the bone. This is undesirable for many reasons, for example, because it does not all the washer 16 to distribute the load in a predictable manner. This may have many detrimental effects including, but not limited to, cracking, chipping, or breaking of the surface of the bone.

FIG. 9 shows the cross-sectional view of the facet screw system in accordance with an exemplary embodiment of the invention. As illustrated, the washer 16 is polyaxially rotatable with respect to the spherical head of the compression member 14. The washer 16 may be provided with a ridge 37 which creates an interference area with the spherical head of the compression member 14. The washer 16 adapted to angulate between 0 to 25 degrees with respect to the compression member 14 and the shaft 12. Also illustrated in FIG. 9, is an undercut 19 that is provided on an upper portion of the shaft 12 so that a removal tool may be used if necessary. The removal tool is capable of engaging with the undercut 19 and configured to remove the shaft 12 from the bone tissue.

In many applications, it is desirable to prevent back out of the screw. One way to do this is by creating an interference area, as described above. In one embodiment, a single continuous ridge or a plurality of ridges may be selectively positioned along the inner surface of the washer 16. One advantage of the ridge 37 is that they create interference between the washer 16 and the screw shaft 12 such that the washer 16 would have to flex out for the screw to back out, or to be unscrewed. This can be accomplished by using a removal tool which engages with the undercut 19 and unscrews the shaft 12 from the bone tissue.

Figure 10:
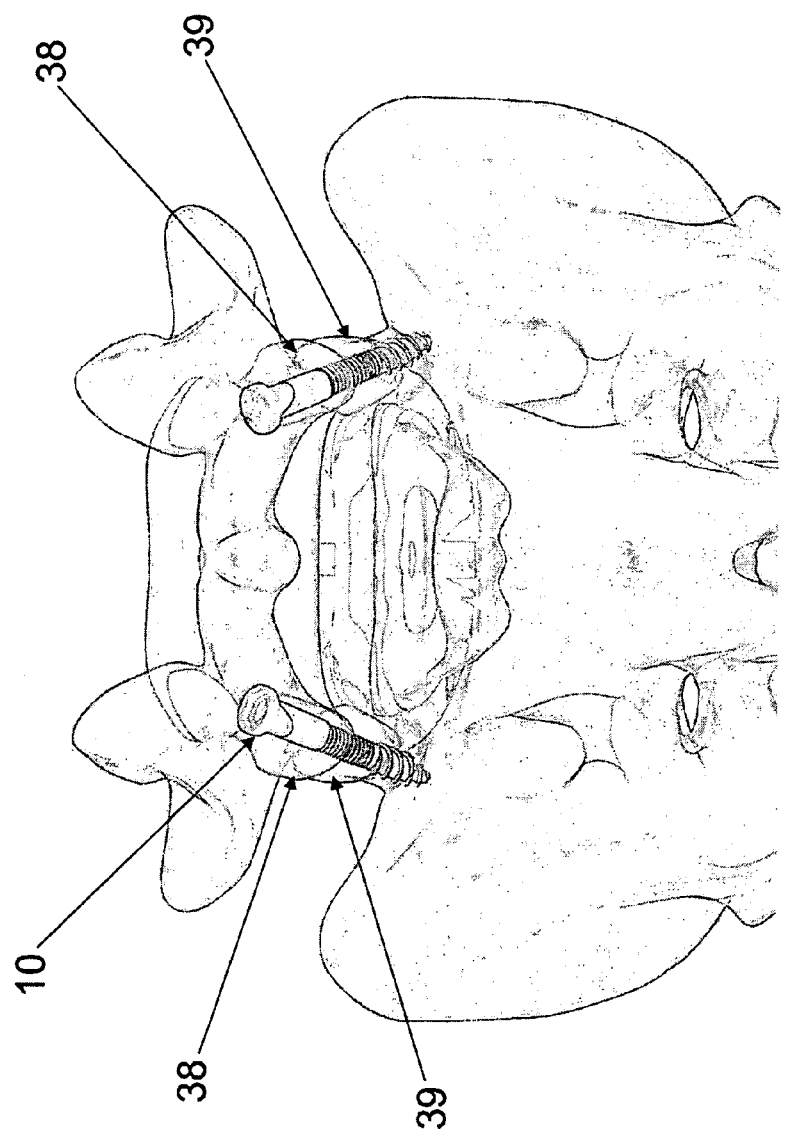
FIGS. 10 and 11 illustrate the prosthetic device positioned in the spine in accordance with an exemplary embodiment of the invention.
Figure 11:
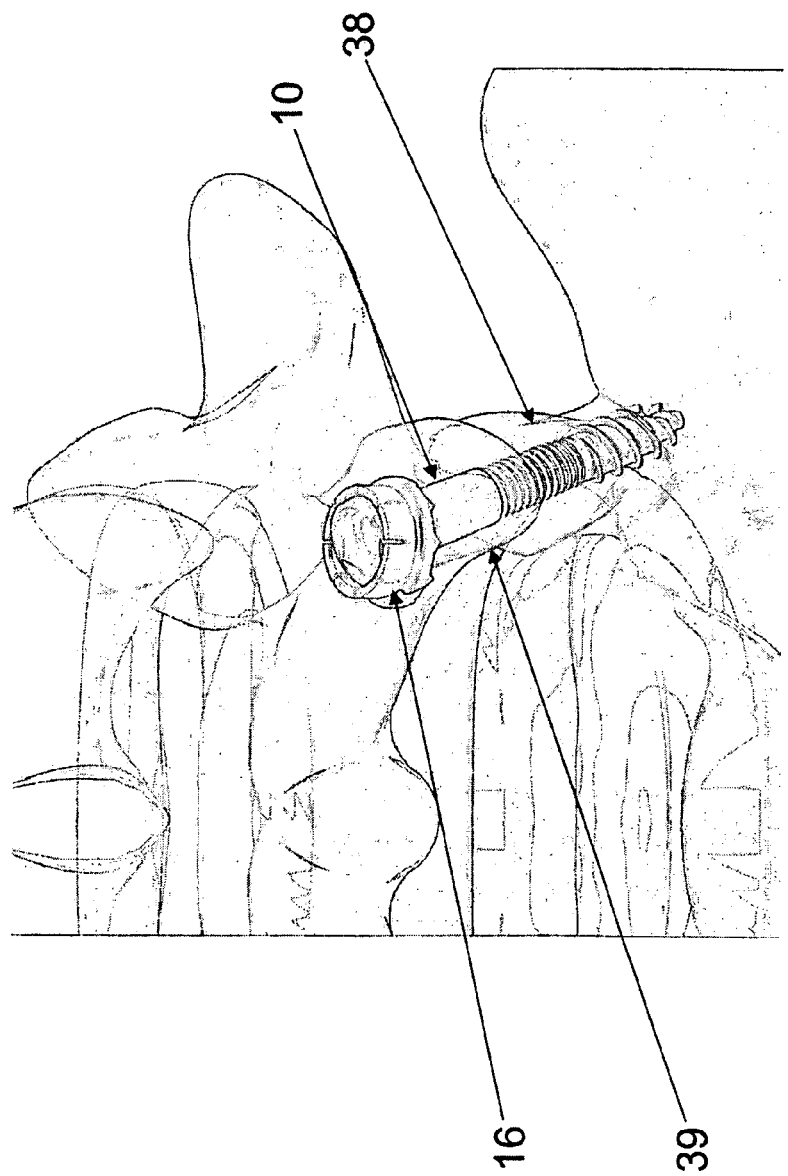

FIGS. 10 and 11 illustrate the facet screw system 10 positioned in the spine according to the preferred embodiment. In the preferred embodiment of the present invention the facet screw 10 is positioned in the bone tissue through the inferior facet 38 and the superior facet 39. As the facet screw 10 is advanced into the bone the inferior and superior facets are compressed together. As a result, the motion between the facets is prohibited thereby enhancing fusion of the spine segment. It is generally preferably to position two facet screw 10 on opposing facet joints on a single level of the vertebrae.

Figure 12:
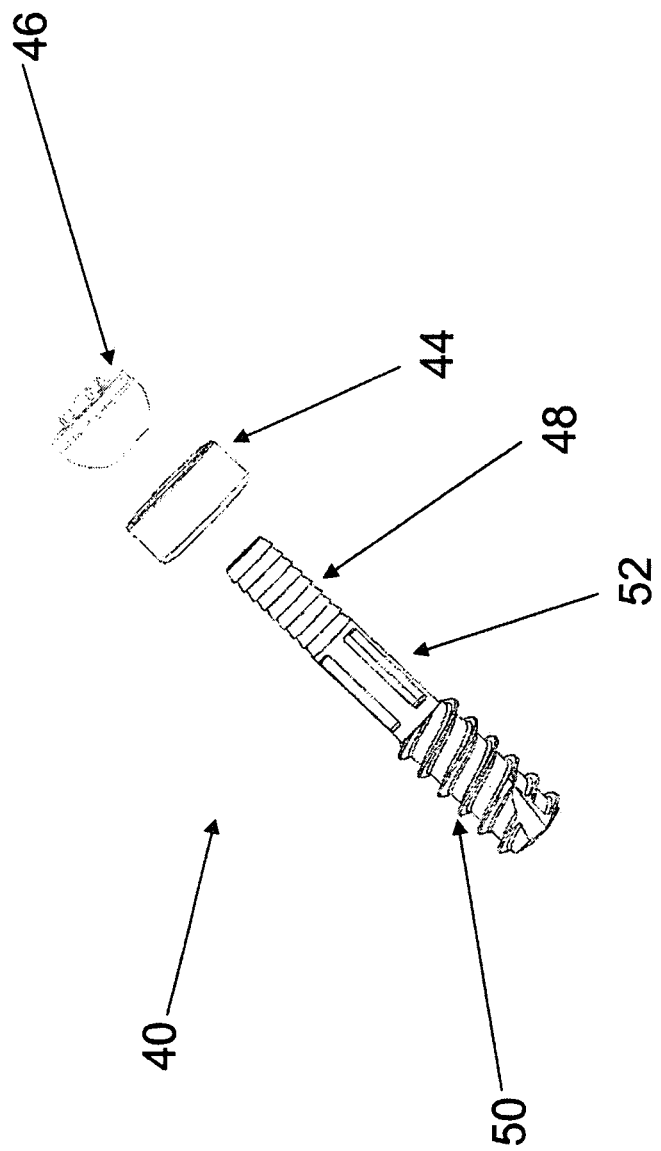
FIG. 12 illustrates another embodiment of the prosthetic device according to the present invention.
Figure 13:
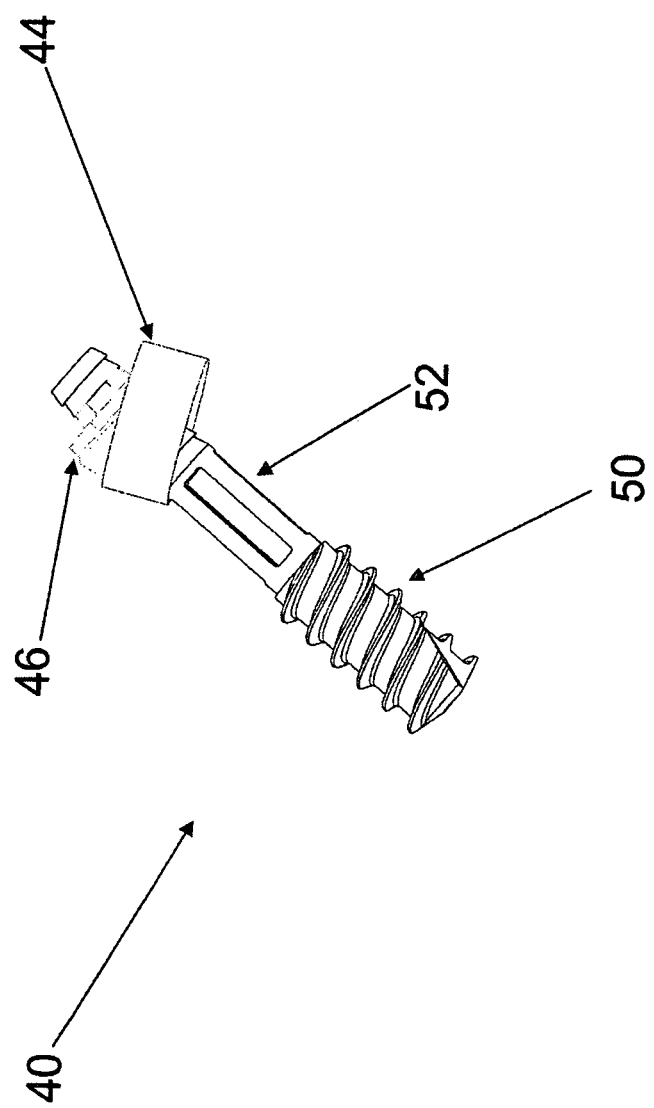
FIG. 13 is another view of the prosthetic device according to the present invention.
Figure 14:
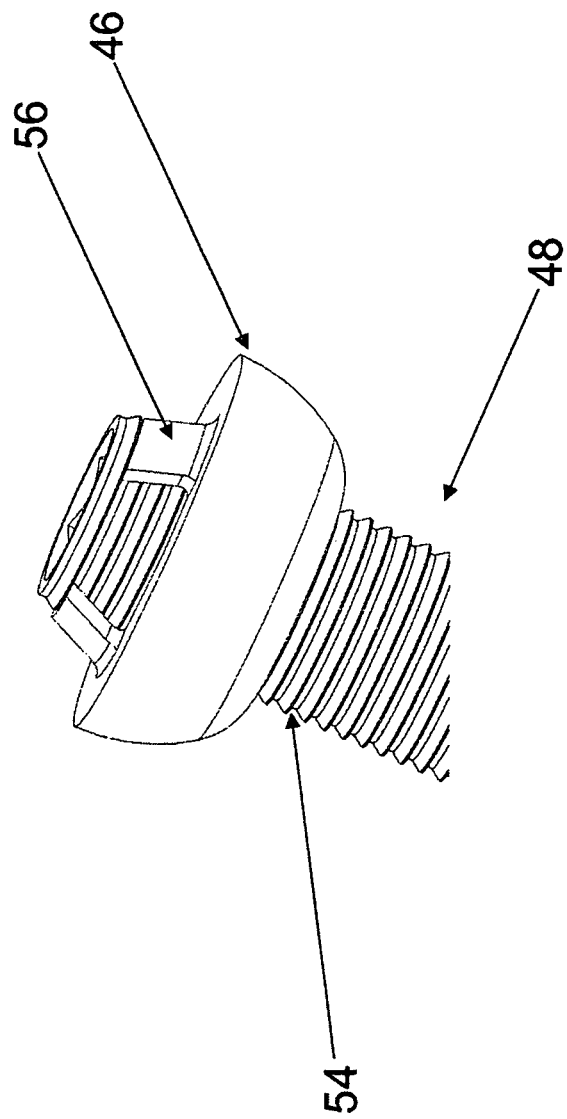
FIG. 14 shows another view of the components of the prosthetic device according to the present invention.

FIG. 12-14 illustrates another embodiment of the facet screw assembly 40 of the present invention. In this particular embodiment, the facet screw assembly 40 is provided with a shaft 42, a washer 44, and a nut 46. The shaft 42 is comprised of a nut engaging portion 48 and the bone engaging portion 50. The shaft is also provided with a bone graft window portion 52 that is positioned between the nut engaging portion 48 and the bone engaging portion 50

The nut engaging portion 48 of the shaft 42 is provided with a plurality of teeth 54 that engages with the nut 46. The nut 46 is configured with at least one teeth engaging protrusion 56. The teeth engaging protrusion 56 is configured so that once the nut 46 can be advanced towards the distal end of the shaft 42, the protrusion 56 engages with the teeth 54 and prohibits the backing out of the nut 46 from the shaft 42. As mentioned in more detail above, the washer 44 is spherical dimensioned and configured so that it may angulate with respect to the nut 46. The washer 44 may also be provided with a plurality of protrusions to engage bone tissue. The plurality of protrusions may be optimally configured to stabilize the facet screw with bone tissue.

While the invention herein disclosed has been described by means of specific embodiments and applications thereof, numerous modifications and variations can be made thereto by those skilled in the art without departing from the scope of the invention as set forth in the claims.

What is claimed is:

1. A facet screw system for surgical implantation into bone tissue, comprising:
    a shaft, the shaft having a bone engaging portion and a compression member engaging portion;
    a compression member having a proximal end and a distal end, the compression member comprising:
        a spherical head portion located at the proximal end and having a recess for engaging with a driving instrument; and
        an elongated coupling portion having internal threads for coupling with the compression member engaging portion of the shaft; and
    a washer having a ridge positioned on a top portion of the washer and plurality of bone engaging protrusions on a bottom portion, the washer being coupled to the spherical head portion of the compression member, wherein the washer comprises a plurality of slits extending along the top portion of the washer, wherein the slits extend to an edge of the top portion of the washer and enable engagement with the compression member, wherein the top portion of the washer including the slits is a flexible portion and the bottom portion of the washer is a bone-engaging portion, wherein an outermost diameter of the bone-engaging portion is greater than an outermost diameter of the top portion, wherein a transition from the outermost diameter of the bone engaging portion to the outermost diameter of the top portion is continuous around its entire periphery,
    wherein a diameter of the spherical head portion of the compression member is greater than a diameter of the bottom portion of the washer,
    wherein the ridge prevents the disengagement of the compression member from the washer, and
    wherein the washer is polyaxially rotatable with respect to the compression member.

2. The facet screw system of claim 1, wherein the facet screw system is cannulated for receiving a guide wire.

3. The facet screw system of claim 1, wherein a flute is provided at a distal end of the shaft.

4. The facet screw system of claim 1, wherein the spherical head of the compression member is configured to receive the driving instrument.

5. The facet screw system of claim 1, wherein the shaft portion comprises a recess for receiving the driving instrument.

6. The bone screw of claim 1, wherein the shaft portion is configured with one type of thread and the compression member engaging portion is configured with another type of thread.

7. The bone screw of claim 1, wherein the screw is made from stainless steel alloys, titanium, titanium based alloys, or polymeric materials.

8. The bone screw of claim 1, wherein the slits do not extend through the bottom portion.

9. The bone screw of claim 1, wherein an outer diameter of the elongated coupling portion of the compression member is substantially the same as an outer diameter of the bone engaging portion of the shaft.

10. The bone screw of claim 1, wherein the washer includes an opening extending through the top portion and the bone engaging portion, and a diameter of the opening being greater in the bone engaging portion relative to the top portion.

11. The bone screw of claim 1, the ridge is positioned on an inner surface of the top portion of the washer.

12. The bone screw of claim 1, wherein the washer includes an opening extending therethrough and the opening has a smallest diameter proximate to the transition.

13. The bone screw of claim 1, wherein the washer includes an opening extending through the top portion and the bone engaging portion, and the opening has a narrower diameter between the top portion and the bone engaging portion.

14. The bone screw of claim 1, wherein the compression member has a reduced inner diameter proximate to the distal end.

15. The bone screw of claim 1, wherein the slits do not extend through the transition.

16. The bone screw of claim 1, wherein the washer is able to angulate up to 25 degrees with respect to the compression member and the shaft.

17. The bone screw of claim 1, wherein the washer extends around an entire periphery of the compression member.

18. A facet screw system for surgical implantation into bone tissue, comprising:
- a shaft, the shaft having a bone engaging portion and a compression member engaging portion;
- a compression member having a proximal end and a distal end, the compression member comprising:
  - a spherical head portion located at the proximal end and having a recess for engaging with a driving instrument; and
  - an elongated coupling portion having internal threads for coupling with the compression member engaging portion of the shaft; and
- a washer having a plurality of bone engaging protrusions on a bottom portion, the washer being coupled to the spherical head portion of the compression member, wherein the washer comprises a plurality of slits extending along a top portion of the washer, wherein the slits extend to an edge of the top portion of the washer and enable engagement with the compression member,
- wherein a diameter of the spherical head portion of the compression member is greater than a diameter of the bottom portion of the washer,
- wherein the washer includes an opening extending through the top portion and the bottom portion, and a diameter of the opening being greater in the bottom portion relative to the top portion and having a narrower diameter positioned between the top and bottom portions, and
- wherein the washer is polyaxially rotatable with respect to the compression member.

* * * * *